US011767349B2

(12) United States Patent
Sumida et al.

(10) Patent No.: US 11,767,349 B2
(45) Date of Patent: Sep. 26, 2023

(54) MODIFIED STREPTOLYSIN O (71) Applicant: TOYOBO CO., LTD., Osaka (JP)

(72) Inventors: Yosuke Sumida, Tsuruga (JP); Hiroaki Kitazawa, Tsuruga (JP); Takahide Kishimoto, Tsuruga (JP)

(73) Assignee: TOYOBO CO., LTD., Osaka (JP)

( * ) Notice: Subject to any disclaimer, the term of this patent is extended or adjusted under 35 U.S.C. 154(b) by 1331 days.

(21) Appl. No.: 16/304,962

(22) PCT Filed: May 26, 2017

(86) PCT No.: PCT/JP2017/019675
§ 371 (c)(1),
(2) Date: Nov. 27, 2018

(87) PCT Pub. No.: WO2017/204325
PCT Pub. Date: Nov. 30, 2017

(65) Prior Publication Data
US 2020/0325186 A1 Oct. 15, 2020

(30) Foreign Application Priority Data

May 27, 2016 (JP) ................. 2016-106150

(51) Int. Cl.
C07K 14/315 (2006.01)
C07K 16/12 (2006.01)
G01N 33/68 (2006.01)

(52) U.S. Cl.
CPC ........ C07K 14/315 (2013.01); C07K 16/1275 (2013.01); G01N 33/6854 (2013.01)

(58) Field of Classification Search
CPC .............. C07K 16/1275; C07K 14/315; G01N 33/6854
See application file for complete search history.

(56) References Cited

U.S. PATENT DOCUMENTS

2002/0182752 A1  12/2002 Miyamoto et al.

FOREIGN PATENT DOCUMENTS

| CN | 102964435 A | 3/2013 | |
|---|---|---|---|
| CN | 102964435 B | 12/2014 | |
| EP | 0369825 A2 | 5/1990 | |
| EP | 2537857 A2 | 12/2012 | |
| JP | H02-242683 A | 9/1990 | |
| JP | 5-184372 A | * 7/1993 | ............... C12N 1/21 |
| JP | H05-184372 A | 7/1993 | |
| JP | H06-502769 A | 3/1994 | |
| JP | H06-237775 A | 8/1994 | |
| JP | 2003-344410 A | 12/2003 | |
| JP | 4704662 B2 | 6/2011 | |
| WO | WO 1993/005155 A1 | 3/1993 | |
| WO | WO 1993/005156 A1 | 3/1993 | |
| WO | WO 2001/092885 A1 | 12/2001 | |

OTHER PUBLICATIONS

Pinkney et al. 1995 (Different Forms of Streptolysin O Produced by Streptococcus pyogenes and by Escherichia coli Expressing Recombination Toxin: Cleavage by Streptococcal cysteine Protease; Infection and Immunity, 1995, vol. 63, No. 7, pp. 2776-2779). (Year: 1995).*
Yamamoto et al. 2001 (Mutational and Comparative Analysis of Streptolysin, an Oxygen-label Streptococcal hemolysin; Biosci. Biotechnol. Biochem. 65(12): 2682-2689 (Year: 2001).*
Pinkney et al. 1995 (Different Forms of Streptolysin O Produced by Streptococcus pyogenes and by Escherichia coli Expressing Recombinant Toxin: Cleavage by Streptococcal cysteine Protease; Infection and Immunity 63(7): 2776-2779) (Year: 1995).*
Nagamune et al., "The Human-Specific Action of Intermedilysin, a Homolog of Streptolysin O, Is Dictated by Domain 4 of the Protein," Microbiol. Immunol., 48(9):677-692 (2004).
Japanese Patent Office, Notice of Reasons for Refusal in Japanese Patent Application No. 2018-519627 (dated May 25, 2021).
Wang et al. (Editors), "Chapter?: Immunological Examination, Section 1:: antistreptolysin 'O' assay," Experimental Diagnostic Methodology, 199-204 (2001).
China National Intellectual Property Administration, First Office Action in Chinese Patent Application No. 201780032199.8 (dated Apr. 26, 2021).
Kodama et al., "Determination of Anti-Streptolysin O Antibody Titer by a New Passive Agglutination Method Using Sensitized Toraysphere Particles," J. Clin. Microbiol., 35(4): 839-842 (1997).
European Patent Office, Extended European Search Report in European Patent Application No. 17802911.2 (dated Dec. 2, 2019).
Kato, "2. Tanpakushitsu no Seishitsu wa?" Mokutekibetsu de Eraberu Tanpakushitsu Hatsugen Protocol, pp. 16-25 (2010).
Kehoe et al., "Nucleotide Sequence of the Streptolysin O (SLO) Gene: Structural Homologies between SLO and Other Membrane-Damaging, Thiol-Activated Toxins," Infect. Immun., 55(12): 3228-3232 (1987).
Pinkney et al., "Different Forms of Streptolysin O Produced by Streptococcus pyogenes and by Escherichia coli Expressing Recombinant Toxin: Cleavage by Streptococcal cysteine Protease," Infect. Immun., 63(7): 2776-2779 (1995).
Weis et al., "Streptolysin O: the C-terminal, tryptophan-rich domain carries functional sites for both membrane binding and self-interaction but not for stable oligomerization," Biochim. Biophys. Acta, 1510(1-2): 292-299 (2001).

(Continued)

*Primary Examiner* — Mary Maille Lyons
(74) *Attorney, Agent, or Firm* — Leydig, Voit & Mayer, Ltd.

(57) ABSTRACT

The invention provides streptolysin O containing a polypeptide comprising an amino acid sequence having deletion of a polypeptide extending from a lysine residue at position 2 of SEQ ID NO: 1 to any of an alanine residue at position 31, a glutamate residue at position 32, a serine residue at position 33, and an asparagine residue at position 34, and also having deletion of any of an isoleucine residue at position 465 to an alanine residue at position 472 of SEQ ID NO: 1 and all of the subsequent amino acid residues, as well as variants thereof and related DNA, vectors, transformants, and methods of use thereof.

8 Claims, 3 Drawing Sheets

Specification includes a Sequence Listing.

(56) References Cited

OTHER PUBLICATIONS

Yamamoto et al., "Mutational and Comparative Analysis of Streptolysin O, an Oxygen-labile *Streptococcal hemolysin*," *Biosci. Biotechnol. Biochem.*, 65(12): 2682-2689 (2001).
Japanese Patent Office, International Search Report in International Patent Application No. PCT/JP2017/019675 (dated Aug. 15, 2017).

* cited by examiner

M: Bench Mark (produced by Invitrogen)
1: N32-C560 His Trap HP purified solution

Fig. 3

M: Bench Mark (produced by Invitrogen)
1: Biokit rSLO

SEQUENCE LISTING

<160> NUMBER OF SEQ ID NOS: 12

<210> SEQ ID NO 1
<211> LENGTH: 571
<212> TYPE: PRT
<213> ORGANISM: Streptococcus pyogenes

<400> SEQUENCE: 1

```
Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30

Ser Asn Lys Gln Asn Thr Ala Ser Thr Glu Thr Thr Thr Thr Asn Glu
        35                  40                  45

Gln Pro Lys Pro Glu Ser Ser Glu Leu Thr Thr Glu Lys Ala Gly Gln
    50                  55                  60

Lys Thr Asp Asp Met Leu Asn Ser Asn Asp Met Ile Lys Leu Ala Pro
65                  70                  75                  80

Lys Glu Met Pro Leu Glu Ser Ala Glu Lys Glu Glu Lys Lys Ser Glu
                85                  90                  95

Asp Lys Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
        115                 120                 125

Glu Thr Ile Glu Asn Phe Val Pro Lys Glu Gly Val Lys Lys Ala Asp
    130                 135                 140
```

```
Lys Phe Ile Val Ile Glu Arg Lys Lys Asn Ile Asn Thr Thr Pro
145                 150                 155                 160

Val Asp Ile Ser Ile Asp Ser Val Thr Asp Arg Thr Tyr Pro Ala
            165                 170                 175

Ala Leu Gln Leu Ala Asn Lys Gly Phe Thr Glu Asn Lys Pro Asp Ala
        180                 185                 190

Val Val Thr Lys Arg Asn Pro Gln Lys Ile His Ile Asp Leu Pro Gly
        195                 200                 205

Met Gly Asp Lys Ala Thr Val Glu Val Asn Asp Pro Thr Tyr Ala Asn
        210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
            245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
        275                 280                 285

Glu Lys Lys Val Met Ile Ala Ala Tyr Lys Gln Ile Phe Tyr Thr Val
        290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
            325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
        355                 360                 365

Leu Lys Gly Thr Asp Val Lys Thr Asn Gly Lys Tyr Ser Asp Ile Leu
        370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
            405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
            435                 440                 445

Arg Thr Glu Tyr Val Glu Thr Thr Ser Thr Glu Tyr Thr Ser Gly Lys
        450                 455                 460

Ile Asn Leu Ser His Arg Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
            485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
            515                 520                 525

Glu Cys Thr Gly Leu Ala Trp Glu Trp Trp Arg Lys Val Ile Asp Glu
        530                 535                 540

Arg Asp Val Lys Leu Ser Lys Glu Ile Asn Val Asn Ile Ser Gly Ser
545                 550                 555                 560
```

Thr Leu Ser Pro Tyr Gly Ser Ile Thr Tyr Lys
             565                 570

<210> SEQ ID NO 2
<211> LENGTH: 1323
<212> TYPE: DNA
<213> ORGANISM: Streptococcus pyogenes

<400> SEQUENCE: 2

| | |
|---|---:|
| atggaatcga acaaacaaaa cactgctagt acagaaacca caacgacaaa tgagcaacca | 60 |
| aagccagaaa gtagtgagct aactactgaa aaagcaggtc agaaaacgga tgatatgctt | 120 |
| aactctaacg atatgattaa gcttgctccc aaagaaatgc cactagaatc tgcagaaaaa | 180 |
| gaagaaaaaa agtcagaaga caaaaaaaag agcgaagaag atcacactga gaaaatcaat | 240 |
| gacaagattt attcactaaa ttataatgag cttgaagtac ttgctaaaaa tggtgaaacc | 300 |
| attgaaaatt ttgttcctaa agaaggcgtt aagaaagctg ataaatttat tgtcattgaa | 360 |
| agaaagaaaa aaatatcaa cactacacca gtcgatattt ccattattga ctctgtcact | 420 |
| gataggacct atccagcagc ccttcagctg gctaataaag gttttaccga aacaaacca | 480 |
| gacgcggtag tcaccaagcg aaacccacaa aaaatcccata ttgatttacc aggtatggga | 540 |
| gacaaagcaa cggttgaggt caatgaccct acctatgcca atgtttcaac agctattgat | 600 |
| aatcttgtta accaatggca tgataattat tctggtggta atacgcttcc tgccagaaca | 660 |
| caatatactg aatcaatggt atattctaag tcacagattg aagcagctct aaatgttaat | 720 |
| agcaaaatct tagatggtac tttaggcatt gatttcaagt cgatttcaaa aggtgaaaag | 780 |
| aaggtgatga ttgcagcata caagcaaatt ttttacaccg tatcagcaaa ccttcctaat | 840 |
| aatcctgcgg atgtgtttga taaatcagtg acctttaaag agttgcaacg aaaaggtgtc | 900 |
| agcaatgaag ctccgccact ctttgtgagt aatgtagcct atggtcgaac tgttttgtc | 960 |
| aaactagaaa caagttctaa agtaatgat gttgaagcgg cctttagtgc agctctaaaa | 1020 |
| ggaacagatg ttaaaacgaa tggaaaatac tctgatatct tagaaaatag ttcatttaca | 1080 |
| gctgtcgttt taggaggaga tgctgcagag cacaataagg tagtcacaaa agactttgat | 1140 |
| gttattagaa acgttatcaa agacaatgct accttcagta gaaaaaaccc agcttatcct | 1200 |
| atttcataca ccagtgtttt ccttaaaaat aataaaattg cgggtgtcaa taacagaact | 1260 |
| gaatacgttg aaacaacatc taccgagtac actagtggaa aaattaacct gtctcatcga | 1320 |
| ggc | 1323 |

<210> SEQ ID NO 3
<211> LENGTH: 1323
<212> TYPE: DNA
<213> ORGANISM: Streptococcus pyogenes

<400> SEQUENCE: 3

| | |
|---|---:|
| atggagtcga acaagcaaaa cactgctagt accgagacca ccacgaccaa tgagcaacca | 60 |
| aagccagaga gtagtgagct gactactgaa aaggcaggcc agaagacgga tgatatgctt | 120 |
| aactctaacg atatgattaa gctggctccg aaagaaatgc cactggaatc tgcagagaag | 180 |
| gaagagaaga agtcagaaga caagaaaaag agcgaagaag atcacactga gaaaatcaat | 240 |
| gacaagattt attcactgaa ttataatgag ctggaagtac tggctaagaa tggtgaaacc | 300 |
| attgaaaatt ttgttcctaa agaaggcgtt aagaaagctg ataaatttat tgtcattgaa | 360 |
| cgcaagaaga agaatatcaa cactactcca gtcgatattt ccatcattga ctctgtcact | 420 |

```
gatcgcacct atccagcagc cctgcagctg gctaataaag gttttaccga aaacaaacca      480
gacgcggtag tcaccaagcg caacccacaa aagatcccta ttgatttacc aggtatggga      540
gacaaagcaa cggttgaggt caatgaccct acctatgcca atgtttcaac agctattgat      600
aatctggtta accaatggca tgataattat tctggtggta atacgctgcc tgcccgcacc      660
caatatactg aatcaatggt atattctaaa tcacagattg aagcagctct gaatgttaat      720
agcaaaatct tagatggtac tttaggcatt gatttcaagt cgatttcgaa aggtgagaag      780
aaggtgatga ttgcagcata caagcaaatc ttctacaccg tatcagcaaa cctgcctaat      840
aatcctgcgg atgtgtttga taaatcagtg acctttaaag agttacaacg caaaggtgtc      900
agcaatgaag ctccgccact ctttgtgagt aacgtagcct atggtcgcac tgtgttcgtc      960
aaactggaaa ccagttctaa gagtaatgat gttgaagcgg cctttagtgc agctctgaaa     1020
ggaaccgatg ttaagacgaa tggcaaatac tctgatatct tagagaatag ttcatttaca     1080
gctgtcgtct taggaggaga tgctgcagag cacaataagg tagtcaccaa agacttcgat     1140
gttattcgca acgttatcaa agacaatgct accttcagtc gcaagaaccc agcttatcct     1200
atttcataca ccagtgtttt ccttaagaat aataagattg cgggtgtcaa taaccgcact     1260
gaatatgttg aaaccacctc taccgagtac actagtggca agattaaccct gtctcatcgc     1320 ggc                                                                    1323

<210> SEQ ID NO 4
<211> LENGTH: 52
<212> TYPE: DNA
<213> ORGANISM: Artificial Sequence
<220> FEATURE:
<223> OTHER INFORMATION: Synthetic Sequence of designed polinucleotide
      described in Example 1

<400> SEQUENCE: 4
agagagcata tgcatcatca tcatcatcat gaatcgaaca acaaaacac tg               52

<210> SEQ ID NO 5
<211> LENGTH: 52
<212> TYPE: DNA
<213> ORGANISM: Artificial Sequence
<220> FEATURE:
<223> OTHER INFORMATION: Synthetic Sequence of designed polinucleotide
      described in Example 1

<400> SEQUENCE: 5
agagagcata tgcatcatca tcatcatcat aaacaaaaca ctgctagtac ag              52

<210> SEQ ID NO 6
<211> LENGTH: 43
<212> TYPE: DNA
<213> ORGANISM: Artificial Sequence
<220> FEATURE:
<223> OTHER INFORMATION: Synthetic Sequence of designed nucleotide
      described in Example 1

<400> SEQUENCE: 6
ccgggggatc cttatttttcc actagtgtac tcggtagatg ttg                       43

<210> SEQ ID NO 7
<211> LENGTH: 40
<212> TYPE: DNA
<213> ORGANISM: Artificial Sequence
<220> FEATURE:
<223> OTHER INFORMATION: Synthetic Sequence of designed nucleotide
      described in Example 1
```

-continued

```
<400> SEQUENCE: 7 ccggggatc cttagttaat ttttccacta gtgtactcgg                                    40

<210> SEQ ID NO 8
<211> LENGTH: 40
<212> TYPE: DNA
<213> ORGANISM: Artificial Sequence
<220> FEATURE:
<223> OTHER INFORMATION: Synthetic Sequence of designed nucleotide
      described in Example 1

<400> SEQUENCE: 8 ccggggatc cttagcctcg atgagacagg ttaatttttc                                    40

<210> SEQ ID NO 9
<211> LENGTH: 36
<212> TYPE: DNA
<213> ORGANISM: Artificial Sequence
<220> FEATURE:
<223> OTHER INFORMATION: Synthetic Sequence of designed nucleotide
      described in Example 1

<400> SEQUENCE: 9 ccggggatc cttatgatcc tgagatgttg acattg                                        36

<210> SEQ ID NO 10
<211> LENGTH: 38
<212> TYPE: DNA
<213> ORGANISM: Artificial Sequence
<220> FEATURE:
<223> OTHER INFORMATION: Synthetic Sequence of designed nucleotide
      described in Example 1

<400> SEQUENCE: 10 ccggggatc cctacttata agtaatcgaa ccgtatgg                                      38

<210> SEQ ID NO 11
<211> LENGTH: 52
<212> TYPE: DNA
<213> ORGANISM: Artificial Sequence
<220> FEATURE:
<223> OTHER INFORMATION: Synthetic Sequence of designed nucleotide
      described in Example 1

<400> SEQUENCE: 11
agagagcata tgcatcatca tcatcatcat gaatcgaaca agcaaaacac tg                     52

<210> SEQ ID NO 12
<211> LENGTH: 43
<212> TYPE: DNA
<213> ORGANISM: Artificial Sequence
<220> FEATURE:
<223> OTHER INFORMATION: Synthetic Sequence of designed nucleotide
      described in Example 1

<400> SEQUENCE: 12 ccggggatc cttacttgcc actagtgtac tcggtagagg tgg                                43
```

MODIFIED STREPTOLYSIN O

CROSS-REFERENCE TO RELATED APPLICATIONS

This patent application is the U.S. national phase of International Patent Application No. PCT/JP2017/019675, filed on May 26, 2017, which claims the benefit of Japanese Patent Application No. 2016-106150, filed May 27, 2016, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 11,074 bytes ASCII (Text) file named "741204SequenceListing.txt," created Nov. 26, 2018.

TECHNICAL FIELD

The present invention relates to streptolysin O (hereinafter also referred to as "SLO" in the present specification) and the use thereof. More specifically, the present invention relates to streptolysin O, a microorganism producing the protein, a method for producing the protein, a method for measuring anti-streptolysin O (hereinafter also referred to as "ASO" in the present specification) using the protein, and the like.

BACKGROUND ART

SLO is a protein having hemolytic activity extracellularly produced by *Streptococcus pyogenes*, and is widely used for raw materials of ASO measuring reagents for the diagnosis of infection with *Streptococcus pyogenes*.

*Streptococcus pyogenes* has been conventionally cultured for the production of SLO. However, the SLO productivity of *Streptococcus pyogenes* was very low, and SLO produced by *Streptococcus pyogenes* had a low purity; thus, there was a problem in that the quality of SLO was not stable. Accordingly, for the purpose of improving productivity and stability, SLO using recombinant *Escherichia coli* has been studied (PTL 1, PTL 2, NPL 1, and NPL 2).

However, NPL 1 reported that when SLO was produced using recombinant *Escherichia coli*, not only full-length type SLO, but also low-molecular-weight type SLO, which was cut in a region at least 50 amino acid residues apart from the C-terminal side, was also produced (NPL 1 refers to full-length type SLO as high-molecular-weight type SLO). In NPL 1, productivity was improved using recombinant *Escherichia coli*; however, it is difficult to control the ratio of full-length type SLO (hereinafter also referred to as "full length type" in the present specification) and low-molecular-weight type SLO by an industrial scale. Thus, the stability of quality has not been achieved.

Furthermore, because SLO is a protein having hemolytic activity, a reduction of hemolytic activity is desired in terms of manufacturers' safety. NPL 2 reports that hemolytic activity is reduced by deleting several amino acid residues at the C-terminal.

CITATION LIST

Patent Literature

PTL 1: JPH05-184372A
PTL 2: JPH06-237775A

Non-Patent Literature

NPL 1: Michael A. Kehoe et al., Infection and Immunity, Vol. 63, No. 7, 2776-2779, 1995
NPL 2: Akira Taketo et al., Biosci. Biotechnol. Biochem., 65 (12), 2682-2689, 2001, 45 (14), 4455-62

SUMMARY OF INVENTION

Technical Problem

The present invention was made in view of the current situation of the prior art. An object of the present invention is to provide SLO that ensures high productivity and has an epitope equivalent to that of natural SLO, without the coexistence of full-length type SLO and low-molecular-weight type SLO. Moreover, in terms of production, there is a demand for SLO having no hemolytic activity and having high thermal stability. Another object of the present invention is to provide SLO also having such characteristics.

Solution to Problem

In order to achieve the above objects, the present inventors conducted extensive research on expression regions of SLO, and consequently found SLO that overcome all the problems. Specifically, in order to prevent the coexistence of full-length type SLO and low-molecular-weight type SLO, modified SLO with deletion of the C-terminal region (hereinafter also referred to as "fragment type" in the present specification) was expressed.

The modified SLO was a cause of concern for the problem of a loss of epitope; however, the present inventors surprisingly confirmed that antigenic activity was not lost even when a region of about 100 amino acid residues on the C-terminal side of full-length type SLO was deleted, and that the antigenic activity per protein was rather more improved than full-length type SLO. This means that there is no important epitope in the region of about 100 amino acid residues deleted from full-length type SLO.

The present inventors also confirmed that the modified SLO had lost hemolytic activity. Furthermore, the present inventors found that the modified SLO had superior thermal stability to that of full-length type SLO. The present invention has thus been completed.

The present invention is based on the above findings and results, and provides the SLO shown below.

[Item 1]
SLO comprising one of the following polypeptides (a) to (d):

(a) a polypeptide comprising an amino acid sequence having deletion of a polypeptide extending from a serine residue at position 2 of SEQ ID NO: 1 to any of an alanine residue at position 31, a glutamate residue at position 32, a serine residue at position 33, and an asparagine residue at position 34, and also having deletion of any of an isoleucine residue at position 465 to an alanine residue at position 472 of SEQ ID NO: 1 and all of the subsequent amino acid residues;

(b) a polypeptide having one or more tags in the N-terminal or C-terminal region of the amino acid sequence shown in (a);

(c) a polypeptide comprising an amino acid sequence having substitution, deletion, insertion, and/or addition of one or more amino acid residues in the amino acid sequence shown in (a), and having antigenic activity against an anti-streptolysin O antibody (ASO); and (d) a polypeptide comprising an amino acid sequence having 90% or more identity with the amino acid sequence shown in (a), and having antigenic activity against an anti-streptolysin O antibody (ASO).

[Item 2]

DNA that is one of the following DNAs (e) to (i):

(e) DNA that encodes the amino acid sequence shown in Item 1;

(f) DNA that comprises a base sequence having deletion of 0, 3, 6, or 9 bases on the 5'-terminal side, except for the atg sequence at the N-terminal, in SEQ ID NO: 2, and also having deletion of 3n (n is an integer of 0 to 7) bases on the 3'-terminal side;

(g) DNA that comprises a base sequence having 80% or more identity with the base sequence represented by SEQ ID NO: 2, and that encodes a polypeptide having antigenic activity against an anti-streptolysin O antibody (ASO);

(h) DNA that hybridizes to a base sequence complementary to the base sequence represented by SEQ ID NO: 2 under stringent conditions, and that encodes a polypeptide having antigenic activity against an anti-streptolysin O antibody (ASO); and (i) DNA that comprises a base sequence having substitution, deletion, insertion, and/or addition of one or more bases in the base sequence represented by SEQ ID NO: 2, and that encodes a polypeptide having antigenic activity against an anti-streptolysin O antibody (ASO).

[Item 3]

DNA that is one of the following DNAs (k) to (n):

(k) DNA that comprises a base sequence having deletion of 0, 3, 6, or 9 bases on the 5'-terminal side, except for the atg sequence at the N-terminal, in SEQ ID NO: 3, and also having deletion of 3n (n is an integer of 0 to 7) bases on the 3'-terminal side;

(l) DNA that comprises a base sequence having 80% or more identity with the base sequence represented by SEQ ID NO: 3, and that encodes a polypeptide having antigenic activity against an anti-streptolysin O antibody (ASO);

(m) DNA that hybridizes to a base sequence complementary to the base sequence represented by SEQ ID NO: 3 under stringent conditions, and that encodes a polypeptide having antigenic activity against an anti-streptolysin O antibody (ASO); and (n) DNA that comprises a base sequence having substitution, deletion, insertion, and/or addition of one or more bases in the base sequence represented by SEQ ID NO: 3, and that encodes a polypeptide having antigenic activity against an anti-streptolysin O antibody (ASO).

[Item 4]

A vector incorporating the DNA according to Item 2 or 3.

[Item 5]

A transformant containing the vector according to Item 4.

[Item 6]

A method for producing the SLO according to Item 1, the method comprising culturing the transformant according to Item 5.

[Item 7]

Crosslinked SLO obtained by crosslinking the SLO according to Item 1.

[Item 8]

Latex particles coated with the SLO according to Item 1 or the crosslinked SLO according to Item 7.

[Item 9]

A method for measuring an anti-streptolysin O antibody (ASO) using the latex particles according to Item 8.

[Item 10]

An anti-streptolysin O antibody (ASO) measuring reagent comprising the latex particles according to Item 8.

Advantageous Effects of Invention

The modified SLO of the present invention is useful as a diagnostic raw material used for ASO reagents having excellent antigenic activity and thermal stability.

BRIEF DESCRIPTION OF DRAWINGS

FIG. 1 shows SDS-PAGE of full-length type streptolysin O and various types of modified streptolysin O.

FIG. 2 shows SDS-PAGE of streptolysin O with a C-terminal at position 560.

FIG. 3 shows SDS-PAGE of streptolysin O produced by Biokit.

FIG. 4 shows a comparison of antigenic activity between various types of streptolysin O.

FIG. 5 shows a comparison of thermal stability between various types of streptolysin O.

FIG. 6 shows a comparison of sensitivity between ASO reagents produced using various types of streptolysin O.

DESCRIPTION OF EMBODIMENTS

Modified Streptolysin O

One embodiment of the present invention is SLO comprising one of the following polypeptides (a) to (d):

(a) a polypeptide comprising an amino acid sequence having deletion of a polypeptide extending from a serine residue at position 2 of SEQ ID NO: 1 to any of an alanine residue at position 31, a glutamate residue at position 32, a serine residue at position 33, and an asparagine residue at position 34, and also having deletion of any of an isoleucine residue at position 465 to an alanine residue at position 472 of SEQ ID NO: 1 and all of the subsequent amino acid residues;

(b) a polypeptide having a tag in the N-terminal or C-terminal region of the amino acid sequence shown in (a);

(c) a polypeptide comprising an amino acid sequence having substitution, deletion, insertion, and/or addition of one or more amino acid residues in the amino acid sequence shown in (a), and having antigenic activity against an anti-streptolysin O antibody (ASO); and (d) a polypeptide comprising an amino acid sequence having 90% or more identity with the amino acid sequence shown in (a), and having antigenic activity against an anti-streptolysin O antibody (ASO).

In the polypeptide (a), SEQ ID NO: 1 is the full length of SLO (full-length type SLO) and comprises 571 amino acids. The amino acid residue at position 1 of SEQ ID NO: 1 is N-terminal methionine. The SLO of the present invention has, on the N-terminal side, deletion of amino acid residues at positions selected from the group consisting of positions 2 to 31, positions 2 to 32, positions 2 to 33, and positions 2 to 34. The 31 residues from the N-terminal are a secretion signal, and are preferably deleted when the SLO of the present invention is intracellularly expressed by gram negative bacteria, such as *Escherichia coli*. In the case of extracellular expression, a secretion signal suitable for the host may be added.

Moreover, the SLO of the present invention has, on the C-terminal side, deletion of amino acid residues at positions selected from the group consisting of positions 465 to 571, positions 466 to 571, positions 467 to 571, positions 468 to 571, positions 469 to 571, positions 470 to 571, positions 471 to 571, and positions 472 to 571.

In the SLO of the present invention, the combination of the N-terminal deletion and the C-terminal deletion is not particularly limited. Preferable examples include a polypeptide comprising amino acid residues from position 32 on the N-terminal side to position 464 on the C-terminal side (in the present specification, such a polypeptide is also represented by "N32-C464" by connecting the numbers indicating the positions of amino acids at both terminals with a hyphen). Other preferable examples include N32-C464, N32-C466, N32-C471, N35-C464, N35-C466, N35-C471, etc.

The SLO of the present invention is not limited to the above (a), and also includes:

(b) a polypeptide having one or more tags in the N-terminal or C-terminal region of the amino acid sequence shown in (a);

(c) a polypeptide comprising an amino acid sequence having substitution, deletion, insertion, and/or addition of one or more amino acid residues (these are also collectively referred to as "modification" in the present specification) in the amino acid sequence shown in (a), and having antigenic activity against an anti-streptolysin O antibody (ASO); and (d) a polypeptide comprising an amino acid sequence having 90% or more identity with the amino acid sequence shown in (a), and having antigenic activity against an anti-streptolysin O antibody (ASO).

This is because if part of the amino acid sequence of a protein is mutated, the mutated protein is often functionally equivalent to the original protein.

In the polypeptide (b), the tags are not particularly limited. Examples include affinity tags, such as His tag, HQ tag, HN tag, HAT tag, GST tag, MBP tag, and Strep (II) tag. It is preferable to select one or more tags from these tags. Of these, His tag, HQ tag, HN tag, HAT tag, Strep (II) tag, etc., are preferable because they hardly affect the function as epitopes. Although the method for inserting a tag into the N-terminal is not particularly limited, it is preferable to insert the tag immediately after the methionine residue at the N-terminal. Alternatively, the tag may be inserted after several amino acid residues. The number of such amino acid residues is not particularly limited; however, the upper limit thereof is preferably 20 or less, more preferably 10 or less, and even more preferably 5 or less, and the lower limit thereof may be 1 or more. Although the method for inserting a tag into the C-terminal is not particularly limited, it is preferable to insert the tag immediately before the stop codon. Alternatively, the tag may be inserted before several amino acid residues. The number of such amino acid residues is not particularly limited; however, the upper limit thereof is preferably 20 or less, more preferably 10 or less, and even more preferably 5 or less, and the lower limit thereof may be 1 or more. When the expression vector skeleton contains a tag, the gene sequence may be suitably deleted.

In the polypeptide (c), the lower limit of the number of "more amino acids" is two. The upper limit is not limited as long as the antigenic activity against ASO is maintained, but is preferably within a range that does not significantly impair the protein spatial configuration of amino acid residues and the antigenic activity against ASO. For example, the upper limit is a number corresponding to less than 20% of all of the amino acids, preferably less than 15%, more preferably less than 10%, even more preferably less than 5%, and still more preferably less than 1%. In other words, the number of amino acids is, for example, 114 or less, preferably 86 or less, more preferably 57 or less, even more preferably 29 or less, still more preferably 20 or less, still more preferably 15 or less, still more preferably 10 or less, still more preferably 5 or less, still more preferably 4 or less, and further still more preferably 3 or less.

In the polypeptide (c), the antigenic activity against ASO, when measured by a "method for measuring antigenic activity of SLO," described later, is 50% or more, preferably 80% or more, more preferably 90% or more, and even more preferably 95% or more, of that of the protein before modification.

In the polypeptide (d), the identity with the amino acid sequence shown in (a) is preferably 80% or more. The identity is preferably 85% or more, more preferably 90% or more, even more preferably 95% or more, still more preferably 98% or more, and further still more preferably 99% or more.

The amino acid sequence identity can be calculated using commercially available analysis tools or those available through electric telecommunication lines (Internet). In the present specification, the identity is determined by selecting blastp in the BLAST website, which is a homology retrieval program published by the National Center for Biotechnology Information (NCBI), and using default parameters.

Whether a certain polypeptide has antigenic activity against ASO is determined according to the "method for measuring antigenic activity of SLO," described later.

The modified protein having antigenic activity against ASO, and the gene thereof, can be obtained by altering the base sequence represented by SEQ ID NO: 2 using a PCR method and a commercially available kit, such as Transformer Mutagenesis Kit (produced by Clonetech), EXOIII/Mung Bean Deletion Kit (produced by Stratagene), QuickChange Site Directed Mutagenesis Kit (produced by Stratagene), or KOD-Plus-Mutagenesis Kit (produced by Toyobo Co., Ltd.).

The antigenic activity of the protein encoded by the obtained gene can be confirmed, for example, by introducing the obtained gene into *Escherichia coli* to produce a transformant, culturing the transformant to produce an enzyme protein, and measuring the transformant, a bacterial cell disrupted liquid of the transformant, or the purified enzyme protein by the "method for measuring antigenic activity of SLO," described later.

DNA Encoding Modified Streptolysin O

Another embodiment of the present invention is DNA that is one of the following DNAs (e) to (i):

(e) DNA that encodes the amino acid sequence of the SLO of the present invention described above;

(f) DNA that comprises a base sequence having deletion of 0, 3, 6, or 9 bases on the 5'-terminal side, except for the atg sequence at the N-terminal, in SEQ ID NO: 2, and also having deletion of 3n (n is an integer of 0 to 7) bases on the 3'-terminal side;

(g) DNA that comprises a base sequence having 80% or more identity with the base sequence represented by SEQ ID NO: 2, and that encodes a polypeptide having antigenic activity against an anti-streptolysin O antibody (ASO);

(h) DNA that hybridizes to a base sequence complementary to the base sequence represented by SEQ ID NO: 2 under stringent conditions, and that encodes a polypeptide having antigenic activity against an anti-streptolysin O antibody (ASO); and (i) DNA that comprises a base sequence having substitution, deletion, insertion, and/or addition of one or more bases in the base sequence represented by SEQ ID NO: 2, and that encodes a polypeptide having antigenic activity against an anti-streptolysin O antibody (ASO).

In the DNA (e), the amino acid sequence of the SLO of the present invention is an amino acid sequence of SLO shown in any of (a) to (d) above. In the DNA of the present invention, when there is a plurality of codons that correspond to the respective amino acids in the above amino acid sequence, the selection thereof is not particularly limited.

In the DNA (f), SEQ ID NO: 2 encodes methionine of the full-length type SLO represented by the amino acid sequence of SEQ ID NO: 1 and a portion corresponding to positions 32 to 471. A sequence having deletion of 3 bases, except for the start codon, on the 5'-terminal side in SEQ ID NO: 2 is supposed to encode N33-C471 in SEQ ID NO: 1. Similarly, a sequence having deletion of 6 bases on the 5'-terminal side is supposed to encode N34-C471, and a sequence having deletion of 9 bases on the 5'-terminal side is supposed to encode N35-C471.

Moreover, a sequence having deletion of 3n (n is 1) bases on the 3'-terminal side is supposed to encode N32-C470 in SEQ ID NO: 1. Similarly, a sequence having deletion of 3n (n is 2) bases on the 3'-terminal side is supposed to encode N32-C469, a sequence having deletion of 3n (n is 3) bases on the 3'-terminal side is supposed to encode N32-C468, a sequence having deletion of 3n (n is 4) bases on the 3'-terminal side is supposed to encode N32-C467, a sequence having deletion of 3n (n is 5) bases on the 3'-terminal side is supposed to encode N32-C466, a sequence having deletion of 3n (n is 6) bases on the 3'-terminal side is supposed to encode N32-C465, and a sequence having deletion of 3n (n is 7) bases on the 3'-terminal side is supposed to encode N32-C464.

In the DNA of the present invention, the combination of the 5'-terminal deletion and the 3'-terminal deletion is not particularly limited. Preferable examples include DNA encoding those mentioned above as examples of the combination of the N-terminal deletion and the C-terminal deletion in the SLO of the present invention.

The DNA of the present invention is not limited to the above (e) and (f), and also includes the following:

(g) DNA that comprises a base sequence having 80% or more identity with the base sequence represented by SEQ ID NO: 2, and that encodes a polypeptide having antigenic activity against an anti-streptolysin O antibody (ASO);

(h) DNA that hybridizes to a base sequence complementary to the base sequence represented by SEQ ID NO: 2 under stringent conditions, and that encodes a polypeptide having antigenic activity against an anti-streptolysin O antibody (ASO); and (i) DNA that comprises a base sequence having substitution, deletion, insertion, and/or addition of one or more bases in the base sequence represented by SEQ ID NO: 2, and that encodes a polypeptide having antigenic activity against an anti-streptolysin O antibody (ASO).

This is because if part of the base sequence of DNA encoding a protein is mutated, and if part of the amino acid sequence of the protein is consequently mutated, the mutated protein is often functionally equivalent to the original protein.

Moreover, this is because when the SLO of the present invention is expressed by incorporating DNA encoding the SLO of the present invention into a host organism (e.g., *Escherichia coli*) other than the organism from which the DNA is derived, the base sequence may be changed depending on the codon usage of the host organism in order to improve expression efficiency. Codons are optimized with reference to, for example, the codon usage database published by Kazusa DNA Research Institute (http://www.kazusa.or.jp/codon/).

For example, when *Escherichia coli* is selected as the host organism, an artificial sequence, such as SEQ ID NO: 3, can be used.

In the DNA (g), the identity with the base sequence represented by SEQ ID NO: 2 is preferably 80% or more. The identity is preferably 85% or more, more preferably 90% or more, even more preferably 95% or more, still more preferably 983 or more, and further still more preferably 99% or more.

The base sequence identity can be calculated using commercially available analysis tools or those available through electric telecommunication lines (Internet). In the present specification, the identity is determined by selecting blastn in the BLAST website, which is a homology retrieval program published by the National Center for Biotechnology Information (NCBI), and using default parameters.

In the DNA (h), the "stringent conditions" generally refer to conditions in which a so-called specific hybrid is formed, and a non-specific hybrid is not formed. Such stringent conditions are known to a person skilled in the art, and can be set with reference to, for example, Molecular Cloning (Third Edition, Cold Spring Harbor Laboratory Press, New York).

In the present specification, the "stringent conditions" refer to, for example, the following conditions: incubation is performed at about 42° C. to about 50° C. using a hybridization liquid (50% formamide, 10×SSC (0.15 M NaCl, 15 mM sodium citrate, pH 7.0), 5×Denhardt solution, 1% SDS, 10% dextran sulfate, 10 µg/ml modified salmon sperm DNA, and 50 mM phosphate buffer (pH 7.5)); then, washing is performed at about 65° C. to about 70° C. using 0.1×SSC and 0.1% SDS.

More preferable stringent conditions are as follows: incubation is performed at about 42° C. to about 50° C. using, as a hybridization liquid, 50% formamide and 5×SSC (0.15 M NaCl, 15 mM sodium citrate, pH 7.0), 1×Denhardt solution, 1% SDS, 10% dextran sulfate, 10 µg/ml modified salmon sperm DNA, and 50 mM phosphate buffer (pH 7.5); then, washing is performed at about 65° C. to about 70° C. using 0.1×SSC and 0.1. SDS.

DNA hybridizing under such conditions may include one in which a stop codon is formed in the middle, and one that has lost activity due to mutation in the active center; however, they can be easily removed by incorporating the DNA into a commercially available active expression vector, allowing the DNA to be expressed in a suitable host, and measuring enzyme activity by a known method.

In the DNA (i), the lower limit of the number of "more amino acids" is two. The upper limit thereof is not limited, as long as the antigenic activity of the polypeptide encoded by the DNA against ASO is maintained, but is preferably within a range that does not significantly impair the protein spatial configuration of amino acid residues and the antigenic activity against ASO. For example, the upper limit is a number corresponding to less than 20% of all of the amino acids of the polypeptide before modification, preferably less than 15%, more preferably less than 10%, even more preferably less than 5%, and still more preferably less than 1%. In other words, the number of amino acids is, for example, 264 or less (the number of bases corresponding to 20% of all of the amino acids), preferably 198 or less (15%), more preferably 132 or less (10%), even more preferably 66 or less (5%), still more preferably 40 or less, still more preferably 20 or less, still more preferably 15 or less, still more preferably 10 or less, still more preferably 5 or less, still more preferably 4 or less, and further sill more preferably 3 or less.

Whether a certain DNA encodes a polypeptide having antigenic activity against ASO is determined by incorporating the DNA into a commercially available active expression vector, allowing the DNA to be expressed in a suitable host, and measuring the antigenic activity of the obtained polypeptide against ASO by the "method for measuring antigenic activity of SLO," described later.

Another embodiment of the present invention is DNA that is one of the following DNAs (k) to (n):

(k) DNA that comprises a base sequence having deletion of 0, 3, 6, or 9 bases on the 5'-terminal side in SEQ ID NO: 3, and also having deletion of 3n (n is an integer of 0 to 7) bases on the 3'-terminal side;

(l) DNA that comprises a base sequence having 80% or more identity with the base sequence represented by SEQ ID NO: 3, and that encodes a polypeptide having antigenic activity against an anti-streptolysin O antibody (ASO);

(m) DNA that hybridizes to a base sequence complementary to the base sequence represented by SEQ ID NO: 3 under stringent conditions, and that encodes a polypeptide having antigenic activity against an anti-streptolysin O antibody (ASO); and (n) DNA that comprises a base sequence having substitution, deletion, insertion, and/or addition of one or more bases in the base sequence represented by SEQ ID NO: 3, and that encodes a polypeptide having antigenic activity against an anti-streptolysin O antibody (ASO).

In the DNAs (k) to (n), SEQ ID NO: 3 is obtained, when DNA encoding the SLO of the present invention is incorporated into a host organism other than the organism from which the DNA is derived, and expressed therein, by changing the base sequence in accordance with the codon usage of the host organism for the purpose of improving expression efficiency. SEQ ID NO: 3 is exemplified as one preferably applied when *Escherichia coli* is selected as the host organism.

The contents described above regarding the DNAs (f) to (i) are applied mutatis mutandis to the explanation of the deletion of bases in the DNAs (k) to (n), the explanation of the method for calculating base sequence identity, the explanation of the stringent conditions, the explanation of the method for confirming whether the DNA encodes a polypeptide having antigenic activity against ASO, the explanation of the upper limit/lower limit of the number of mutations, etc.

Method for Producing Streptolysin O, Etc.

Another embodiment of the present invention is a vector incorporating the DNA of the present invention, a transformant containing the vector, or a method for producing the SLO, the method comprising culturing the transformant.

The SLO of the present invention can be easily produced by inserting the gene thereof into a suitable vector to prepare a recombinant vector, transforming a suitable host cell with this recombinant vector to prepare a transformant, and culturing the transformant.

The vector is not particularly limited, as long as it is capable of replicating and retaining, or autonomously replicating in various host cells, such as prokaryotic cells and/or eukaryotic cells. Examples include plasmid vectors, phage vectors, viral vectors, and the like. The preparation of a recombinant vector may be performed by a conventional method, although it is not particularly limited thereto. For example, a recombinant vector can be easily prepared by linking the gene of the SLO of the present invention to a vector mentioned above using suitable restriction enzymes and ligases, and optionally further a linker or adapter DNA. Moreover, a gene fragment produced by amplification using a DNA polymerase in which one base is added to the amplification end, such as Taq polymerase, can be joined to a vector by TA cloning.

Moreover, the host cells may be conventionally known host cells, and are not particularly limited as long as the recombinant expression system is established. Preferable examples include microorganisms, such as *Escherichia coli, Bacillus subtilis, Actinomyces, Aspergillus*, and yeast, as well as insect cells, animal cells, higher plants, and the like; more preferably microorganisms; and particularly preferably *Escherichia coli* (e.g., K12 strain and B strain). The preparation of a transformant may be performed by a conventional method, although it is not particularly limited thereto. When the host is *Escherichia coli*, usable examples thereof include *Escherichia coli* C600, *Escherichia coli* HB101, *Escherichia coli* DH5a, *Escherichia coli* JM109, and *Escherichia coli* BL21; and examples of the vector include pBR322, pUC19, pBluescript, pQE, and pET. When the host is yeast, examples thereof include *Saccharomyces cerevisiae, Schizosaccharomyces pombe, Candida utilis*, and *Pichia pastoris*; and examples of the vector include pAUR101, pAUR224, and pYE32. When the host is a filamentous fungal cell, examples thereof include *Aspergillus oryzae* and *Aspergillus niger*.

When the obtained transformant is cultured for a certain period of time under suitable culture conditions depending on the host cells, the SLO of the present invention is expressed from the incorporated gene, and accumulated in the transformant.

The SLO of the present invention accumulated in the transformant can be used without purification, but may be used after purification. The purifying method is not particularly limited, and a conventionally known method can be used. For example, the purification can be carried out by homogenizing the transformant after culture or a cultured product thereof in a suitable buffer, performing ultrasonication, surfactant treatment, etc., to obtain a cell extract, and treating the cell extract by a suitable combination of isolation techniques generally used for isolation and purification of proteins. Examples of such isolation techniques include, but are not limited to, methods using differences in solubility, such as salting-out and solvent precipitation methods; methods using differences in molecular weight, such as dialysis, ultrafiltration, gel filtration, non-denaturing polyacrylamide gel electrophoresis (PAGE), and sodium dodecyl sulfate-polyacrylamide gel electrophoresis (SDS-PAGE); methods using electrification, such as ion-exchange chromatography and hydroxyapatite chromatography; methods using specific affinity, such as affinity chromatography; methods using hydrophobic differences, such as reversed-phase high-pressure liquid chromatography; methods using differences in isoelectric points, such as isoelectric focusing; and the like. A purified enzyme preparation can be obtained, for example, by performing isolation and purification by gel filtration using Sephadex gel (produced by GE Healthcare Bioscience) etc., column chromatography on DEAE Sepharose CL-6B (produced by GE Healthcare Bioscience), Octyl Sepharose CL-6B (produced by GE Healthcare Bioscience), or the like.

Crosslinking of Streptolysin O

Another embodiment of the present invention is crosslinked SLO obtained by crosslinking the SLO of the present invention.

SLO may be covalently bonded to a bifunctional substance for stabilization. Therefore, the modified SLO of the present invention may also be covalently bonded to a bifunctional substance. Examples of such bifunctional substances include glutaraldehyde and carbodiimide. Because Schiff bases formed by the reaction of the aldehyde groups of glutaraldehyde and amino groups are unstable in an aqueous solution, a reductive amination reaction may be performed using sodium boron cyanohydride or sodium boron hydride. Covalent bonding is physically irreversible; specifically, the covalent bond is not affected by pH or temperature changes. In crosslinking treatment, it is necessary to set the type of buffer, pH, treatment temperature, treatment time, SLO concentration, and bifunctional substance concentration; however, conditions that do not have adverse effects on the SLO and the crosslinked SLO can be used, and are not particularly limited. Examples are shown below. Examples of the buffer include acetate buffers, Good's buffers such as MES buffers and PIPES buffers, phosphate buffers, Tris-HCl buffers, borate buffers, glycine buffers, and the like. The pH is preferably in the range of 5 to 11, and more preferably 6 to 10. The temperature is preferably 4° C. to 40° C., and more preferably 10° C. to 30° C. The protein concentration is preferably 0.1 mg/ml to 100 mg/ml, and more preferably 1 mg/ml to 10 mg/ml. The reaction time is preferably 1 minute to 24 hours, and more preferably 10 minutes to 5 hours. The concentration of the bifunctional substance in the crosslinking reaction is preferably 0.0001% to 1%, and more preferably 0.0013 to 0.1%. After the crosslinking reaction, glycine at a final concentration of 0.1% to 10% may be added in order to prevent the further reaction of uncrosslinked glutaraldehyde.

Latex Particles

Another embodiment of the present invention is latex particles coated with the SLO or crosslinked SLO of the present invention.

The latex particles used in the present invention are not particularly limited. Examples include polystyrene, a styrene-styrene sulfonate copolymer, a methacrylic acid polymer, an acrylic acid polymer, an acrylonitrile-butadiene-styrene copolymer, a vinyl chloride-acrylic ester copolymer, polyvinyl acetate acrylate, and the like. The average particle diameter of the latex particles is not particularly limited; however, latex particles having an average particle diameter of 0.05 µm to 1.0 µm are suitably selected, in consideration of the concentration of the test substance in the test sample, or the detection sensitivity of the measuring equipment.

Latex Particles in which Antigen is Immobilized

The method for immobilizing modified SLO in the latex particles of the present invention is not particularly limited, and a physical adsorption (hydrophobic bond) method, a chemical bond method, etc., can be suitably selected. In the physical adsorption (hydrophobic bond) method, polyhapten can be formed for adsorption. In the chemical bond method, a binding functional group, such as a maleimide group, can be introduced into an antigen. When an antigen is adsorbed to latex, it is necessary to set the type of buffer, pH, treatment temperature, treatment time, and SLO concentration; however, these are not particularly limited. Examples are shown below. Examples of the buffer include acetate buffers, Good's buffers such as MES buffers and PIPES buffers, phosphate buffers, Tris-HCl buffers, borate buffers, glycine buffers, and the like. The pH is preferably in the range of 5 to 11, and more preferably 6 to 10. The temperature is preferably 4° C. to 40° C., and more preferably 10° C. to 30° C. The SLO concentration is preferably 0.01 mg/ml to 30 mg/ml, and more preferably 0.1 mg/ml to 3 mg/ml. The reaction time is preferably 1 minute to 24 hours, and more preferably 10 minutes to 5 hours. In order to prevent non-specific reactions and increase the stability of the immunoassay reagent itself, SLO may be adsorbed to latex in a state where one or more additives are contained, although it is not particularly limited thereto.

Measuring Reagent

Another embodiment of the present invention is a method for measuring ASO using the latex particles of the present invention, or an ASO measuring reagent comprising the latex particles of the present invention.

The present invention also includes immunoassay using the immunoassay reagent of the present invention. The immunoassay of the present invention can be performed by a general method, and is not particularly limited as long as it uses the immunoassay reagent of the present invention. For example, the immunoassay reagent of the present invention is added to a medium containing a substance to be measured, and aggregation generated by bonding between the substance to be measured and the antigen immobilized on the latex particles contained in the immunoassay reagent of the present invention due to an antigen-antibody reaction is observed optically or visually. The lower limit of the pH during reaction is preferably 5, and more preferably 6; and the upper limit of the pH during reaction is preferably 10, and more preferably 9. The lower limit of the temperature during reaction is preferably 4° C., and more preferably 20° C.; and the upper limit of the temperature during reaction is preferably 50° C., and more preferably 40° C. The reaction time may be suitably determined.

As the above medium, various suitable buffers are used depending on the type of substance to be measured. Such buffers may be those that do not inactivate the substance to be measured, and that have an ion concentration and pH that do not inhibit the antigen-antibody reaction. Examples of such buffers include known buffers, such as phosphate buffers, glycine buffers, borate buffers, Tris-HCl buffers, and various Good's buffers. These buffers may be used singly or in combination of two or more.

In order to increase the sensitivity of the reaction, the above medium may contain known water-soluble additives, such as polyethylene glycol, carboxyl methyl cellulose, methyl cellulose, dextran, polyvinyl pyrrolidone, polyglycosylethyl methacrylate, pullulan, dextran, elsinan, and like water-soluble polymers. Further, for the purpose of improving specificity, reagent stability, etc., the medium may also contain proteins, such as albumin, casein, and gelatin, or decomposed products or modified products thereof; quaternary ammonium salts, such as choline chloride; EDTA, polyanions, chaotropic ions ($Cl^-$, $I^-$, $SCN^-$, etc.), amino acids, surfactants, and the like. Moreover, the medium may also contain a preservative, such as sodium azide or phenylmethanesulfonyl fluoride.

The method for detecting the degree of aggregation generated by the above antigen-antibody reaction is not particularly limited. For example, the degree of aggregation can be detected by optical observation or visual observation. Specifically, as a method for optically detecting the degree of aggregation of insoluble carriers, for example, an increase or decrease in scattered light intensity, absorbance, or transmitted light intensity is measured. As a determination method by visual observation, for example, a sample and the immunoassay reagent of the present invention are mixed on a determination plate, the plate is swung for 1 to 5 minutes, and then the presence of aggregation is determined. Alternatively, an image may be photographed and subjected to image processing.

Method for Measuring Antigenic Activity of SLO

In the present invention, the method for measuring the antigenic activity of SLO is performed under the following conditions. In this method for measuring antigenic activity, latex particles in which SLO is immobilized, and SLO (a test substance) in a test sample are allowed to compete to inhibit the formation of an immune complex of the latex particles and antibody, and the test substance (antigen) is measured by the degree of inhibition of aggregation of the latex particles in association with the inhibition of immune complex formation. The term "antigenic activity" used in the present specification specifically means a value measured by the following method, unless otherwise specifically noted.

Reagent

ASO Latex X1 "Seiken" R1 reagent (buffer), produced by Denka Seiken Co., Ltd.

ASO Latex X1 "Seiken" R2 reagent (latex (SLO-adsorbed latex) suspension), produced by Denka Seiken Co., Ltd.

ASO standard solution (500 IU/ml), produced by Denka Seiken Co., Ltd.

Measuring Sample

A measuring sample is prepared by mixing an ASO standard solution (500 IU/ml, produced by Denka Seiken Co., Ltd.), physiological saline, and an SLO solution at a ratio of 5:4:1. Moreover, the SLO solution was used after being diluted with 20 mM phosphate buffer solution (pH 7.5), as necessary. In a blind test, 20 mM phosphate buffer solution (pH 7.5) for diluting SLO is used in place of the SLO solution.

Measurement Method

Using the measuring sample, the R1 reagent, and the R2 reagent, the antigenic activity of SLO in the sample against ASO (SAU/mg: Streptolysin O Antigenic Unit/mg) was measured using a Hitachi 7170 Autoanalyzer under the following conditions.

Sample: 3 μL (containing an ASO standard solution (250 IU/ml))
R1 reagent: 70 μL
R2 reagent: 120 μL
Measurement method: Two-point end method (19-34)
Dominant wavelength: 570 nm
Complementary wavelength: 800 nm Antigenic activity (SAU/mg)={(measured value (BLANK)−measured value (TEST)}×10×dilution ratio of SLO solution/protein concentration (mg/ml)

The present invention is described in more detail below with reference to Examples.

Example 1

Example 1: Cloning of SLO Gene

Using the artificially synthesized gene (Accession number: NC003485) shown in SEQ ID NO: 2 as a template, various SLO genes were amplified using the primers shown in Table 1 (in Table 1, Fw represents a forward primer, and Rv represents a reverse primer). Specifically, a gene encoding SLO in which the start codon and a histidine tag were followed by a glutamate residue at position 32, and a lysine residue at position 464 as the terminal (which is also referred to as "N32-C464") was amplified using the primers of SEQ ID NOs: 4 and 6. Similarly, genes encoding various SLOs, i.e., N32-C466, N32-C471, N35-C464, N35-C466, N35-C471, N32-C560, and N32-C571, were amplified using the primers of SEQ ID NOs: 4 and 7, SEQ ID NOs: 4 and 8, SEQ ID NOs: 5 and 6, SEQ ID NOs: 5 and 7, SEQ ID NOs: 5 and 8, SEQ ID NOs: 4 and 9, and SEQ ID NOs: 4 and 10, respectively. Restriction enzyme site NdeI was added to the N-terminal side of these primers, and restriction enzyme site BamHI was added to the C-terminal side. This DNA fragment was cut with restriction enzymes NdeI and BamHI, and mixed with vector plasmid pBSK cut with the same enzymes. A ligation reagent (Ligation high, produced by Toyobo Co., Ltd.) in the same amount as the mixed solution was added, and incubation was performed, thereby carrying out ligation. Recombinant plasmids pBSKSLO (N32-C464, N32-C466, N32-C471, N35-C464, N35-C466, N35-C471, N32-C560, and N32-C571) designed to be able to express a large amount of SLO gene was obtained in this manner.

TABLE 1

| Expression construct | Primer sequence | | Sequence No. |
|---|---|---|---|
| N32-C464 | Fw | AGAGAGCATATGCATCATCATCATCATCATGAATCGAACAAACAAAACACTG | 4 |
| | Rv | CCGGGGGATCCTTATTTTCCACTAGTGTACTCGGTAGATGTTG | 6 |
| N32-C466 | Fw | AGAGAGCATATGCATCATCATCATCATCATGAATCGAACAAACAAAACACTG | 4 |
| | Rv | CCGGGGGATCCTTAGTTAATTTTCCACTAGTGTACTCGG | 7 |
| N32-C471 | Fw | AGAGAGCATATGCATCATCATCATCATCATGAATCGAACAAACAAAACACTG | 4 |
| | Rv | CCGGGGGATCCTTAGCCTCGATGAGACAGGTTAATTTTTC | 8 |
| N35-C464 | Fw | AGAGAGCATATGCATCATCATCATCATCATAAAGAAAACACTGCTAGTACAG | 5 |
| | Rv | CCGGGGGATCCTTATTTTCCACTAGTGTACTCGGTAGATGTTG | 6 |
| N35-C466 | Fw | AGAGAGCATATGCATCATCATCATCATCATAAAGAAAACACTGCTAGTACAG | 5 |
| | Rv | CCGGGGGATCCTTAGTTAATTTTCCACTAGTGTACTCGG | 7 |
| N35-C471 | Fw | AGAGAGCATATGCATCATCATCATCATCATAAACAAAAGAGTGCTAGTACAG | 5 |
| | Rv | CCGGGGGATCCTTAGCCTCGATGAGACAGGTTAATTTTTC | 8 |
| N32-C560 | Fw | AGAGAGCATATGCATCATCATCATCATCATGAATCGAACAAACAAAACACTG | 4 |
| | Rv | CCGGGGGATCCTTATGATCCTGAGATGTTGACATTG | 9 |
| N32-C571 | Fw | AGAGAGCATATGCATCATCATCATCATCATGAATCGAACAAACAAAACACTG | 4 |
| | Rv | CCGGGGGATCCCTACTTATAAGTAATCGAACCGTATGG | 10 |

Example 2

Example 2: Expression and Purification of Various SLO Genes in E. coli

Figure 1:
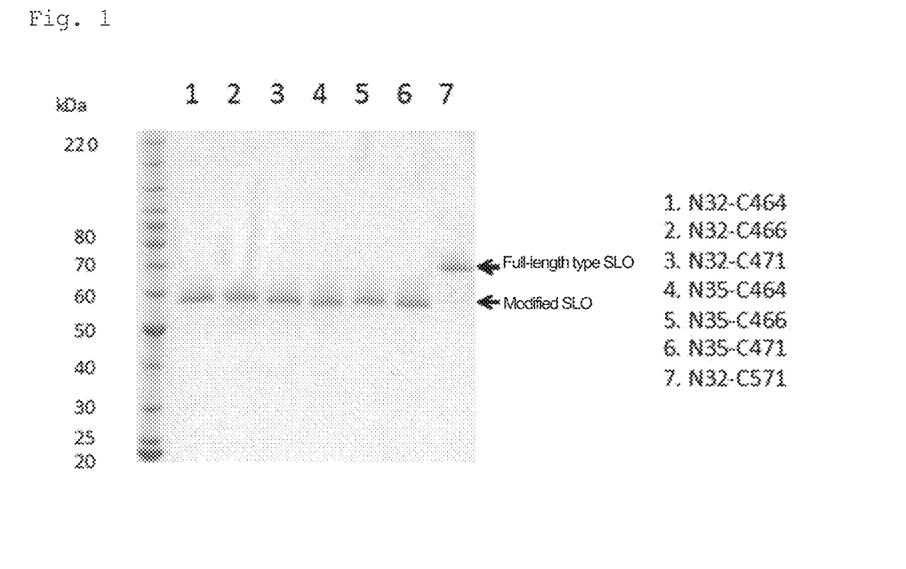
Figure 2:
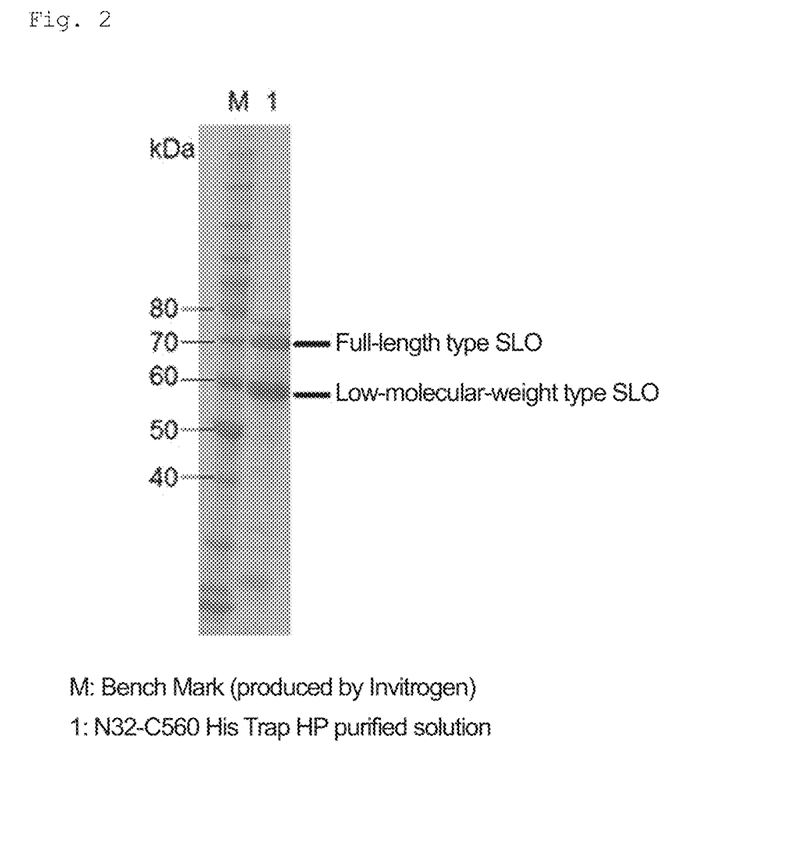

Using the various plasmids constructed in Example 1, Escherichia coli JM 109 strain competent cells (Competent High JM109, produced by Toyobo Co., Ltd.) were transformed according to the protocol attached to this product to thereby obtain transformants. The colonies of each of the obtained transformants were inoculated in 5 mL of LB liquid medium (containing 50 μg/mL ampicillin) that had been sterilized in a test tube, and aerobically cultured by shaking at 30° C. for 16 hours. The obtained culture solution, which was used as a seed culture solution, was inoculated in 100 mL of TB medium (containing 1 mM IPTG and 50 μg/mL ampicillin) placed in a 500-ml Sakaguchi flask, and cultured at a shaking speed of 180 rpm at 30° C. for 20 hours. The thus-obtained bacterial cells were collected by centrifugal separation, suspended in 25 mM phosphate buffer solution (pH 7.5) containing 20 mM imidazole, and crushed with glass beads. The obtained crude enzyme was applied to a 1-mL HisTrap HP column (produced by GE Healthcare Bioscience) equilibrated with 25 mM phosphate buffer solution (pH 7.5) containing 20 mM imidazole, and eluted with 25 mM phosphate buffer solution (pH 7.5) containing 500 mM imidazole to remove the expression construct of N32-C560, thereby obtaining a streptolysin solution of high purity. Further, in order to improve the purity, isolation and purification was performed using a 5-mL CM-FF column (GE healthcare Bioscience), thereby succeeding in improving the purity so that impure proteins could not be detected on SDS-PAGE level. FIG. 1 shows the results of SDS-PAGE using each sample prepared above. In the expression construct of N32-C560 resulting from the deletion of 11 C-terminal residues, low-molecular-weight type SLO, which seemed to be a degradation product, was confirmed, in addition to the band of the full-length type, in the eluted fraction of a 1-mL HisTrap HP column (produced by GE Healthcare Bioscience) (FIG. 2).

Example 3

Example 3: Evaluation of Hemolytic Activity

The hemolytic activity of each SLO solution prepared in Example 2 was measured. As the measurement method, first, 50 μl of SLO diluted with a PBS solution containing 20 mM cysteine was added to 1 ml of rabbit defibrinated blood (produced by Nippon Bio-Test Laboratories Inc.) diluted to 2% with PBS solution, and the mixture was reacted at 37° C. for 1 hour. The protein concentration of each SLO solution during measurement was 1.0 mg/ml. As shown in Table 2, absorption at 541 nm ($A_{541}$) showing the degree of hemolysis was detected for the full-length type SLO (N32-C571). There was no significant difference between the modified SLOs and Blank, and it was confirmed that the modified SLOs had lost hemolytic activity.

TABLE 2

| Sample | $A_{541}$ | Hemolytic activity |
|---|---|---|
| Blank | 0.085 | – |
| N32 C464 (1.0 mg/ml) | 0.081 | – |
| N32-C466 (1.0 mg/ml) | 0.083 | – |
| N32-C471 (1.0 mg/ml) | 0.086 | – |
| N35-C464 (1.0 mg/ml) | 0.087 | – |
| N35-C466 (1.0 mg/ml) | 0.089 | – |
| N35-C471 (1.0 mg/ml) | 0.079 | – |
| N32-C571 (1.0 mg/ml) | 1.920 | + |

Example 4

Example 4: Measurement of Antigenic Activity

Figure 3:
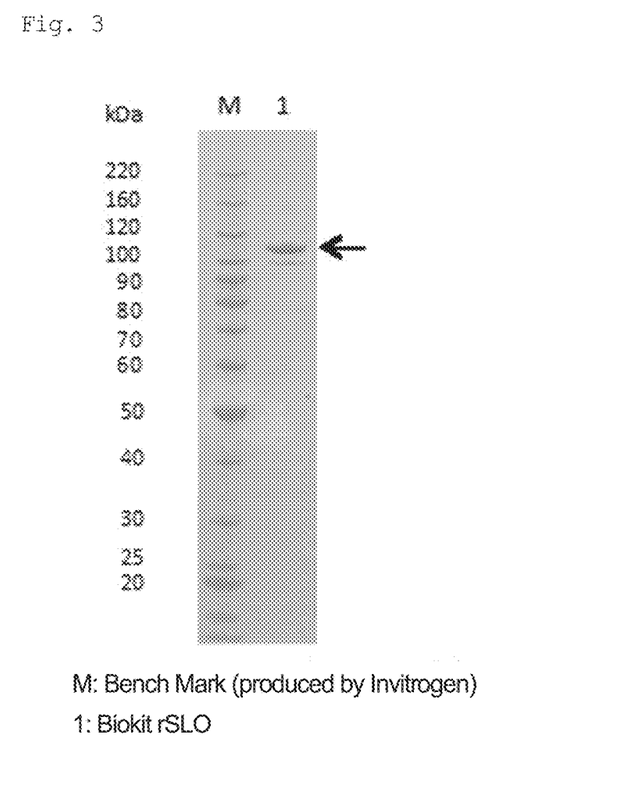
Figure 4:
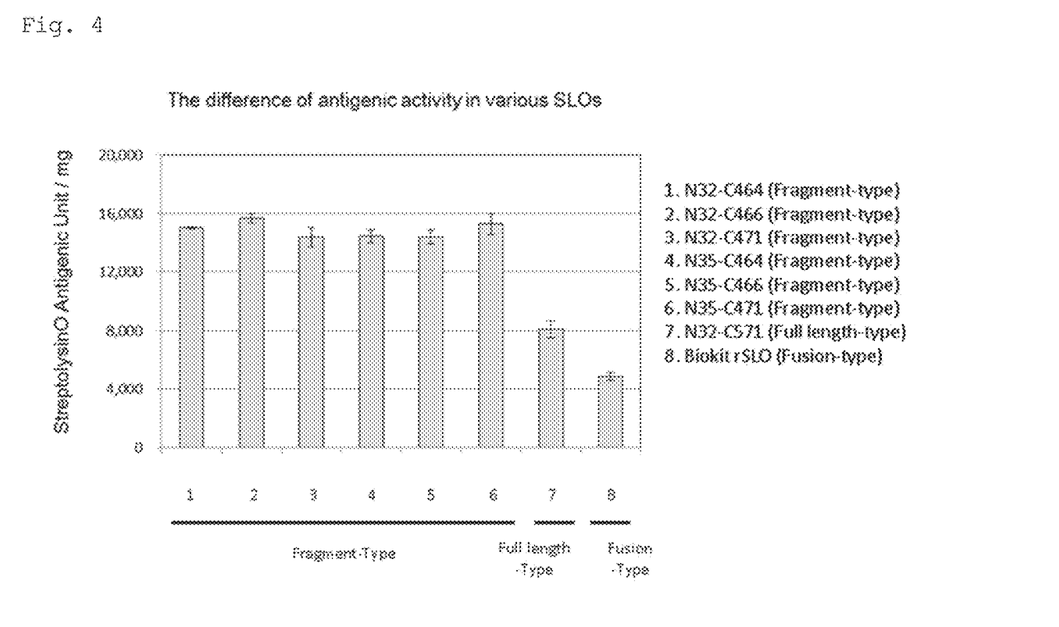

Antigenic activity was measured using each of the SLO solutions prepared in Example 2 and SLO produced by Biokit (code: T3000-5258). FIG. 3 shows the SDS-PAGE results of the Biokit SLO. It was confirmed that the molecular weight of the Biokit SLO was about 40 kDa higher than that of the full-length type SLO. Since this result suggested the possibility of a fused protein, the Biokit SLO is also referred to as "fusion type" in the present specification. FIG. 4 shows the measurement results of antigenic activity. The protein concentration of the SLO solution during measurement was 0.08 mg/ml for the modified SLOs, 0.11 mg/ml for the full-length type SLO, and 0.16 mg/ml for the Biokit SLO. The modified SLOs showed higher antigenic activity than the full-length type SLO. These results indicate that there is no important epitope in the deleted region of about 100 amino acid residues. It was also confirmed that the antigenic activity of the Biokit SLO was lower than that of the full-length type SLO.

Example 5

Example 5: Evaluation of Thermal Stability

Figure 5:
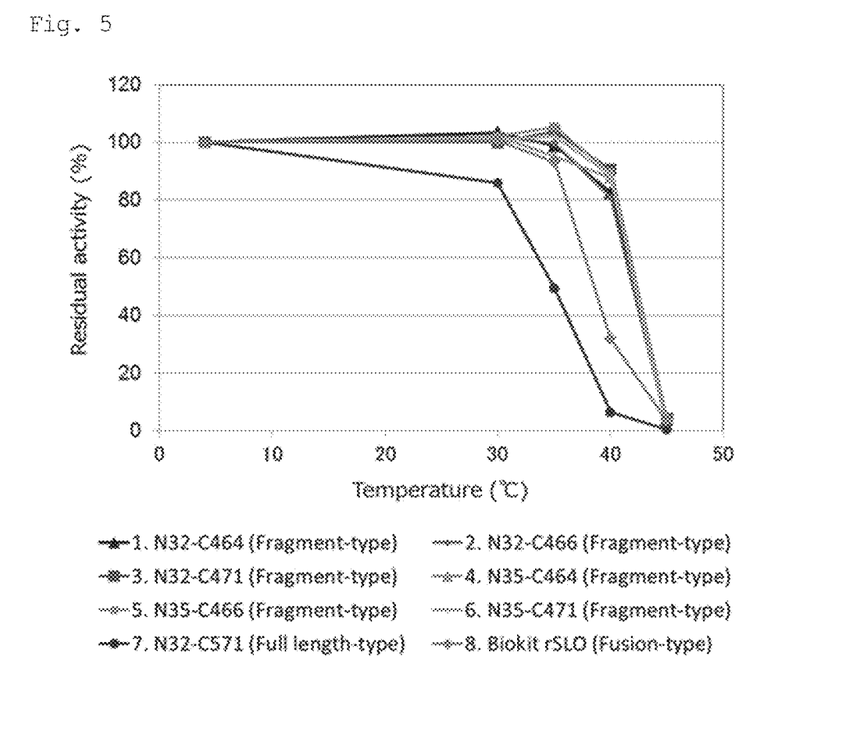

Using each of the SLO solutions prepared in Example 2 and SLO produced by Biokit (code: T3000-5258), thermal stability was evaluated by measuring antigenic activity after heat treatment. FIG. 5 shows the results. The protein concentration of each SLO solution during measurement was 2.0 mg/ml, and treatment was performed at each temperature for 6 hours. Then, antigenic activity was measured to evaluate thermal stability. As a result, it was confirmed that the modified SLOs had higher thermal stability than the full-length type SLO, and practically acquired beneficial characteristics. It was also confirmed that the thermal stability of the modified SLOs was superior to that of the Biokit SLO (code: T3000-5258).

Example 6

Example 6: Codon Usage Optimization in *Escherichia coli* Expression

Codon usage was optimized to improve expression levels in *Escherichia coli*. The artificially synthesized sequence is represented by SEQ ID NO: 3. An expression plasmid was constructed in the same manner as in Examples 1 and 2. Table 3 shows primers used to construct the plasmid. Using the constructed plasmid, *Escherichia coli* JM 109 strain competent cells (Competent high JM109, produced by Toyobo Co., Ltd.) were transformed according to the protocol attached to this product, thereby obtaining a transformant. The colonies of the obtained transformant were inoculated in 5 mL of LB liquid medium (containing 50 μg/mL of ampicillin) that had been sterilized in a test tube, and aerobically cultured by shaking at 30° C. for 16 hours. The obtained culture solution, which was used as a seed culture solution, was inoculated in 100 mL of TB medium (containing 1 mM IPTG and 50 μg/mL ampicillin) placed in a 500-ml Sakaguchi flask, and cultured at a shaking speed of 180 rpm at 30° C. for 20 hours. As a result, expression of about 300 mg/L of modified SLO was confirmed. This value corresponded to about twice the value before the optimization of codon usage. It was confirmed that the productivity was improved by codon sequence optimization.

TABLE 3

| Expression construct | Primer sequence | | Sequence No. |
|---|---|---|---|
| N32-C464 | Fw | AGAGAGCATATGCATCATCATCATCA TCATGAATCGAACAAGCAAAACACTG | 11 |
| | Rv | CCGGGGATCCTTACTTGCCACTAGT GTACTCGGTAGAGGTGG | 12 |

Example 7: Evaluation of Sensitivity in Latex Turbidimetry Reagent

Figure 6:
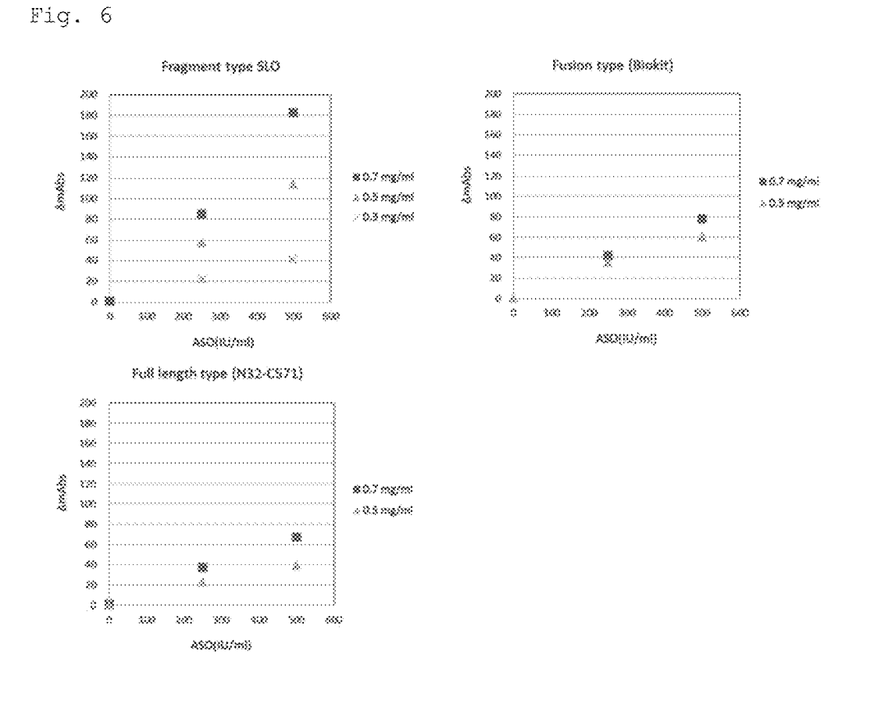

Each of the SLO solutions prepared in Example 2 and SLO produced by Biokit (code: T3000-5258) were prepared to a concentration of 2.2 mg/mL, and 25% glutaraldehyde solution (produced by Sigma, code: G5882) was added to a final concentration of 0.1%. Next, the solution was mechanically stirred at room temperature for 1 hour. Thereafter, glycine was added to a final concentration of 0.1%. Next, the solution was mechanically stirred at room temperature for 30 minutes, and then stored at 4° C. overnight. Thereafter, the protein concentration was determined by the Bradford method, and the solution was coated on latex particles. The coating conditions were as follows. A buffer comprising 50 mM borate buffer (pH 8.2) was mixed so that the final concentration of crosslinked SLO was 0.3 to 0.7 mg/ml, as shown in FIG. 6, and the coating treatment was performed at 37° C. for 1 hour. Thereafter, a washing step including centrifugation, supernatant removal, and suspension was repeated twice using 50 mM glycine buffer (pH 8.2) containing 150 mM NaCl and 0.5% BSA, thereby obtaining a second reagent in a latex turbidimetry reagent. As a first reagent, a buffer comprising 20 mM Tris-HCl buffer (pH 8.2), 150 mM NaCl, and 0.5% BSA was prepared, and the sensitivity of the latex reagent was evaluated. As the measurement method, the first and second reagents were combined, and the formation of particle aggregates dependent on the ASO concentration was confirmed using a Hitachi 7170 Autoanalyzer. Specifically, 240 µL of the first reagent was added to 3 µL of ASO solutions having a concentration of 0 (IU/mL), 250 (IU/mL), or 500 (IU/mL), and each mixture was warmed at 37° C. for 5 minutes; then, 60 µL of the second reagent was added, and each mixture was stirred. Then, absorbance changes (ΔmAbs) associated with the formation of aggregates for 5 minutes were measured at a dominant wavelength of 546 nm and a complementary wavelength of 800 nm. As a result, when the SLO concentration during coating on latex was 0.7 mg/ml and the ASO concentration was 500 (IU/ml), ΔmAbs of the Biokit SLO was 78.1, and ΔmAbs of the full-length type SLO was 66.9, whereas ΔmAbs of the modified SLO of the present invention was 183.1, which was about 2 to 3 times higher than that of the other SLOs. Moreover, when the SLO concentration was 0.5 mg/ml and the ASO concentration was 500 (IU/ml), ΔmAbs of the Biokit SLO was 60.2, and ΔmAbs of the full-length type SLO was 38.9, whereas ΔmAbs of the modified SLO of the present invention was 114.2, which was about 2 to 3 times higher than that of the other SLOs. These results demonstrate that the modified SLO of the present invention has high antigenic activity per protein, and that the amount of SLO used for the production of ASO reagents can be reduced.

INDUSTRIAL APPLICABILITY

The modified SLO of the present invention is useful as a diagnostic raw material used for ASO reagents having excellent antigenic activity and thermal stability.

The invention claimed is:

1. A Streptolysin O consisting of a polypeptide having one or more tags in the N-terminal or C-terminal region of an amino acid sequence selected from position 32 to position 464 of SEQ ID NO: 1, position 32 to position 466 of SEQ ID NO: 1, position 32 to position 471 of SEQ ID NO: 1, position 35 to position 464 of SEQ ID NO: 1, position 35 to position 466 of SEQ ID NO: 1, and position 35 to position 471 of SEQ ID NO: 1.

2. A crosslinked streptolysin O obtained by crosslinking the streptolysin O consisting of:

(a) a polypeptide consisting of an amino acid sequence selected from position 32 to position 464 of SEQ ID NO: 1, position 32 to position 466 of SEQ ID NO: 1, position 32 to position 471 of SEQ ID NO: 1, position 35 to position 464 of SEQ ID NO: 1, position 35 to position 466 of SEQ ID NO: 1, and position 35 to position 471 of SEQ ID NO: 1, or (b) a polypeptide having one or more tags in the N-terminal or C-terminal region of the amino acid sequence shown in (a).

3. A latex particle coated with the crosslinked streptolysin O according to claim 2.

4. An anti-streptolysin O antibody (ASO) measuring reagent comprising the latex particle according to claim 3.

5. A latex particle coated with the streptolysin O consisting of:
(a) a polypeptide consisting of an amino acid sequence selected from position 32 to position 464 of SEQ ID NO: 1, position 32 to position 466 of SEQ ID NO: 1, position 32 to position 471 of SEQ ID NO: 1, position 35 to position 464 of SEQ ID NO: 1, position 35 to position 466 of SEQ ID NO: 1, and position 35 to position 471 of SEQ ID NO: 1, or (b) a polypeptide having one or more tags in the N-terminal or C-terminal region of the amino acid sequence shown in (a).

6. An anti-streptolysin O antibody (ASO) measuring reagent comprising the latex particle according to claim 5.

7. A method for producing the streptolysin O according to claim 1, the method comprising culturing the transformant containing a vector incorporating the DNA that is amplified from a base sequence represented by SEQ ID NO: 3 as a template by using primers of SEQ ID NOs: 11 and 12.

8. A method for producing the streptolysin O according to claim 1, the method comprising culturing a transformant containing a vector incorporating DNA that is either
(a) DNA that encodes the polypeptide of claim 1, or
(b) DNA that is amplified from a base sequence represented by SEQ ID NO: 2 as a template by using primers selected from SEQ ID NOs: 4 and 6, SEQ ID NOs: 4 and 7, SEQ ID NOs: 4 and 8, SEQ ID NOs: 5 and 6, SEQ ID NOs: 5 and 7, and SEQ ID NOS: 5 and 8.

\* \* \* \* \*